United States Patent
Kim et al.

(10) Patent No.: US 11,834,415 B2
(45) Date of Patent: Dec. 5, 2023

(54) ADHESIVE COMPOSITION FOR SEMICONDUCTOR CIRCUIT CONNECTION AND ADHESIVE FILM INCLUDING THE SAME

(71) Applicant: LG CHEM, LTD., Seoul (KR)

(72) Inventors: Ju Hyeon Kim, Daejeon (KR); Junghak Kim, Daejeon (KR); Seunghee Nam, Daejeon (KR); Kwang Joo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 840 days.

(21) Appl. No.: 16/769,786

(22) PCT Filed: Apr. 17, 2019

(86) PCT No.: PCT/KR2019/004651
§ 371 (c)(1),
(2) Date: Jun. 4, 2020

(87) PCT Pub. No.: WO2019/203572
PCT Pub. Date: Oct. 24, 2019

(65) Prior Publication Data
US 2020/0308121 A1 Oct. 1, 2020

(30) Foreign Application Priority Data

Apr. 17, 2018 (KR) .................. 10-2018-0044654
Apr. 15, 2019 (KR) .................. 10-2019-0043931

(51) Int. Cl.
| | |
|---|---|
| *C07D 233/58* | (2006.01) |
| *C08J 5/18* | (2006.01) |
| *C09J 133/08* | (2006.01) |
| *C09J 163/00* | (2006.01) |
| *C09J 171/12* | (2006.01) |
| *H01L 23/00* | (2006.01) |

(52) U.S. Cl.
CPC .............. *C07D 233/58* (2013.01); *C08J 5/18* (2013.01); *C09J 133/08* (2013.01); *C09J 163/00* (2013.01); *C09J 171/12* (2013.01); *H01L 24/29* (2013.01); *C08J 2333/08* (2013.01); *C08J 2363/00* (2013.01); *C08J 2371/12* (2013.01); *C08J 2433/08* (2013.01); *C08J 2463/00* (2013.01); *C08J 2471/12* (2013.01); *H01L 2224/2919* (2013.01); *H01L 2924/066* (2013.01); *H01L 2924/0665* (2013.01)

(58) Field of Classification Search
CPC ....... C07D 233/58; C08L 63/00; C08L 63/04; C08L 63/06; C08L 63/08; C08L 63/10; C09J 163/00; C09J 163/04; C09J 163/06; C09J 163/08; C09J 163/10
See application file for complete search history.

(56) References Cited

U.S. PATENT DOCUMENTS

| | | |
|---|---|---|
| 4,528,358 A | 7/1985 | Kleeberg et al. |
| 6,822,341 B1 | 11/2004 | Ahsan |
| 2003/0069331 A1 | 4/2003 | Teiichi et al. |
| 2007/0054114 A1 | 3/2007 | Kumakura |
| 2010/0203307 A1 | 8/2010 | Komiyatani et al. |
| 2011/0006419 A1 | 1/2011 | Hirano |
| 2012/0281376 A1 | 11/2012 | Koyama et al. |
| 2013/0059942 A1 | 3/2013 | Ono et al. |
| 2013/0158231 A1 | 6/2013 | Kamegaya et al. |
| 2014/0205816 A1 | 7/2014 | Maejima |
| 2017/0198182 A1 | 7/2017 | Kim et al. |
| 2017/0233610 A1 | 8/2017 | Kim et al. |
| 2018/0265758 A1 | 9/2018 | Kim et al. |

FOREIGN PATENT DOCUMENTS

| | | | |
|---|---|---|---|
| EP | 2071000 A1 | 6/2009 | |
| EP | 2242090 A1 | 10/2010 | |
| JP | H01-096278 A | 4/1989 | |
| JP | 2012-046715 A | 3/2012 | |
| JP | 2014-197675 A | 10/2014 | |
| JP | 2016-029152 A | 3/2016 | |
| JP | 2016-029153 A | 3/2016 | |
| JP | 2016-183317 A | 10/2016 | |
| KR | 10-2006-0120646 A | 11/2006 | |
| KR | 10-0669134 B1 | 1/2007 | |
| KR | 10-1343156 B1 | 12/2013 | |
| KR | 10-1493625 B1 | 2/2015 | |
| KR | 10-2017-0035609 A | 3/2017 | |
| TW | 200829671 A | 7/2008 | |
| TW | 200942594 A | 10/2009 | |
| TW | 201309772 A | 3/2013 | |
| TW | 201641651 A | 12/2016 | |
| WO | WO-2017052289 A1 * | 3/2017 | ........... C08G 59/621 |

OTHER PUBLICATIONS

International Search Report issued for International Application No. PCT/KR2019/004651 dated Aug. 2, 2019, 4 pages.
Kudo, K. et al., "Imidazole Derivatives with an Intramolecular Hydrogen Bond as Thermal Latent Curing Agents for Thermosetting Resins", ACS Macro Lett., 2015, vol. 4, 10, pp. 1085-1088.
Extended European Search Report dated Jan. 20, 2021, of the corresponding European Patent Application No. 19789001.5, 11 pages.

* cited by examiner

*Primary Examiner* — Zachary M Davis
(74) *Attorney, Agent, or Firm* — ROTHWELL, FIGG, ERNST & MANBECK, P.C.

(57) ABSTRACT

The present disclosure relates to an adhesive resin composition for bonding semiconductors, including: a thermoplastic resin; a thermosetting resin; a curing agent; and a compound having a specific structure, and an adhesive film for semiconductors including the same.

14 Claims, No Drawings

ADHESIVE COMPOSITION FOR SEMICONDUCTOR CIRCUIT CONNECTION AND ADHESIVE FILM INCLUDING THE SAME

CROSS-REFERENCE TO RELATED APPLICATION

This application is a 35 U.S.C. 371 National Phase Entry Application from PCT/KR2019/004651 filed on Apr. 17, 2019, designating the United States and which claims the benefits of Korean Patent Applications No. 10-2018-0044654 filed on Apr. 17, 2018 and No. 10-2019-0043931 filed on Apr. 15, 2019, the disclosures of which are incorporated herein by reference in their entirety.

TECHNICAL FIELD

The present disclosure relates to an adhesive composition for semiconductor circuit connection and an adhesive film for semiconductors.

BACKGROUND OF THE INVENTION

Recently, as the tendency toward miniaturization, high functionalization, and capacity enlargement of electronic devices has been expanding and the need for densification and high integration of the semiconductor package has rapidly increased, the size of semiconductor chips has become larger and larger. In terms of improvement of an integration degree, a stack package method in which chips are stacked in multiple stages is increasingly used.

In addition, semiconductors using TSV (Through Silicon Via) have been developed and signals are transmitted through bump bonding. For the bump bonding, a thermo-compression bonding technique is generally applied. In this case, a thermosetting property of the adhesive in the thermo-compression bonding technique affects package manufacturing processability and package reliability.

A non-conductive paste (NCP) in the form of a paste had been developed as an adhesive for filling between the respective TSV layers, but a pitch of the bump was narrowed and the filling became difficult. In order to overcome this problem, a non-conductive film (NCF), which is in the form of a film, is being developed.

When the thermo-compression bonding is performed for the bump bonding, the adhesive should be cured rapidly at a high temperature and the curing should be suppressed at room temperature, thereby improving storage stability. Catalysts play an important role in controlling the degree of cure for these adhesives, and a thermally-latent catalyst has been developed for this purpose.

BRIEF SUMMARY OF THE INVENTION

The present disclosure provides an adhesive composition for semiconductor circuit connection, which can be cured within a short period of time at a high temperature during thermo-compression bonding and has excellent storage stability at room temperature.

The present disclosure also provides an adhesive film including the adhesive composition for semiconductor circuit connection.

The present disclosure provides an adhesive resin composition for bonding semiconductors, including: a thermoplastic resin; a thermosetting resin; a curing agent; and a compound represented by the following Chemical Formula 1.

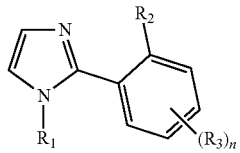

[Chemical Formula 1]

In Chemical Formula 1, $R_1$ is hydrogen, a C1 to C10 alkyl group, or a C6 to C20 aryl group, $R_2$ is an organic functional group containing a functional group capable of hydrogen bonding, $R_3$ is hydrogen, a halogen, a C1 to C10 alkyl group, or a C6 to C20 aryl group, and n is 1 to 4 as a substitution number of $R_3$.

More specifically, in Chemical Formula 1, $R_1$ may be hydrogen or a benzene group, and $R_2$ may be a hydroxyl group, a carboxyl group, a carbonyl group, a formyl group, or an amine group.

The adhesive resin composition for bonding semiconductors may include 0.1 to 15 parts by weight of the compound of Chemical Formula 1 based on 100 parts by weight of a total amount of the thermoplastic resin; the thermosetting resin; the curing agent; and the compound of Chemical Formula 1.

The thermoplastic resin may include at least one polymer resin selected from the group consisting of polyimide, polyether imide, polyester imide, polyamide, polyether sulfone, polyether ketone, polyolefin, polyvinyl chloride, phenoxy, reactive butadiene acrylonitrile copolymer rubber, and a (meth)acrylate-based resin.

The thermosetting resin may include at least one selected from the group consisting of a solid epoxy resin and a liquid epoxy resin.

The curing agent may include a phenolic resin having a softening point of 70° C. or higher.

The present disclosure also provides an adhesive film for semiconductors, including the adhesive resin composition for bonding semiconductors.

Advantageous Effects

According to the present disclosure, an adhesive composition for semiconductor circuit connection, which can be cured within a short period of time at a high temperature during thermo-compression bonding and has excellent storage stability at room temperature, and an electrodeposited film for semiconductors, are provided.

DETAILED DESCRIPTION OF THE INVENTION

Hereinafter, the adhesive composition for semiconductor circuit connection and the electrodeposited film for semiconductors according to the exemplary embodiments of the present disclosure will be described in more detail. However, the following examples are only to illustrate the invention, and the scope of the invention is not limited thereto.

According to an embodiment of the present disclosure, an adhesive resin composition for bonding semiconductors is provided, including: a thermoplastic resin; a thermosetting resin; a curing agent; and a compound represented by the following Chemical Formula 1.

[Chemical Formula 1]

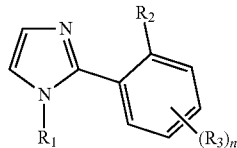

In Chemical Formula 1, $R_1$ is hydrogen, a C1 to C10 alkyl group, or a C6 to C20 aryl group, $R_2$ is an organic functional group containing a functional group capable of hydrogen bonding, $R_3$ is hydrogen, a halogen, a C1 to C10 alkyl group, or a C6 to C20 aryl group, and n is 1 to 4 as a substitution number of $R_3$.

The present inventors conducted studies on components that can be used for bonding or packaging semiconductor devices. As a result, they found through experiments that when a composition or an adhesive film including the compound of Chemical Formula 1 is applied as a material for semiconductor circuit connection, it can be cured within a short period of time at a high temperature during thermo-compression bonding and has excellent storage stability at room temperature, thereby completing the present invention.

Specifically, the compound of Chemical Formula 1 includes an organic functional group containing a functional group capable of hydrogen bonding at $R_2$, which may delay the curing reaction by deactivating the catalyst at room temperature at which hydrogen bonding is performed, and may activate the catalyst by breaking down the hydrogen bond at a temperature above the curing temperature during thermo-compression bonding. Accordingly, the adhesive resin composition for bonding semiconductors of the embodiment can be rapidly cured at a high temperature and can be stored at room temperature for a long period of time.

As described above, in Chemical Formula 1, $R_1$ may be hydrogen, a C1 to C10 alkyl group, or a C6 to C20 aryl group, $R_2$ may be an organic functional group containing a functional group capable of hydrogen bonding, $R_3$ may be hydrogen, a halogen, a C1 to C10 alkyl group, or a C6 to C20 aryl group, and n may be 1 to 4 as a substitution number of $R_3$. More specifically, in Chemical Formula 1, $R_1$ may be hydrogen or a benzene group, and $R_2$ may be a hydroxyl group, a carboxyl group, a carbonyl group, a formyl group, or an amine group.

The adhesive resin composition for bonding semiconductors may include 0.1 to 15 parts by weight, or 0.5 to 10 parts by weight, of the compound of Chemical Formula 1 based on 100 parts by weight of a total amount of the thermoplastic resin; the thermosetting resin; the curing agent; and the compound of Chemical Formula 1.

When the weight of the compound of Chemical Formula 1 is too low based on 100 parts by weight of a total amount of the thermoplastic resin; the thermosetting resin; the curing agent; and the compound of Chemical Formula 1, it is difficult for the curing reaction to proceed. Therefore, the degree of cure is not secured or the reaction temperature range becomes wide, resulting in the loss of the rapid curing property, which is present at a specific temperature.

When the weight of the compound of Chemical Formula 1 is too high based on 100 parts by weight of a total amount of the thermoplastic resin; the thermosetting resin; the curing agent; and the compound of Chemical Formula 1, some of the catalyst may be activated even at room temperature, so that storage stability of the film may not be secured.

According to an embodiment of the present disclosure, the adhesive composition for semiconductor circuit connection may further include a thermoplastic resin, a thermosetting resin, and an inorganic filler in addition to the compound of Chemical Formula 1.

In addition, the adhesive composition for semiconductor circuit connection may further include a thermosetting resin, a thermoplastic resin, a curing agent, and an inorganic filler in addition to the compound of Chemical Formula 1.

As the thermosetting resin, the thermoplastic resin and the curing agent contained in the adhesive resin composition for bonding semiconductors of the embodiment that are conventionally known components in the field of the adhesive composition for semiconductor circuit connection can be applied.

The examples of the thermosetting resin are not particularly limited, and for example, an epoxy resin may be preferably used.

Specifically, the epoxy resin may be at least one selected from the group consisting of a bisphenol-based epoxy resin, a biphenyl-based epoxy resin, a naphthalene-based epoxy resin, a fluorene-based epoxy resin, a phenol novolac-based epoxy resin, a cresol novolac-based epoxy resin, a tris(hydroxyphenyl)methane-based epoxy resin, a tetraphenyl-methane-based epoxy resin, a dicyclopentadiene type of epoxy resin, and a dicyclopentadiene-modified phenol type of epoxy resin.

Examples of the bisphenol-based epoxy resin include a bisphenol A type of epoxy resin, a bisphenol F type of epoxy resin, a bisphenol S type of epoxy resin, a hydrogenated bisphenol A type of epoxy resin, and a bisphenol AF type of epoxy resin.

For example, when two types of epoxy resins are used as the thermosetting resin, a mixture of an epoxy resin in a liquid phase at 10 to 35° C. and an epoxy resin in a solid phase at 10 to 35° C. at a weight ratio of 1:0.1 to 1:5 may be used.

When the content of the solid epoxy resin is less than 0.1 parts by weight based on the liquid epoxy resin, excessive resin may flow out during a die attachment process to cause contamination, and the adhesive layer may be very sticky to cause deterioration of a pick-up property. On the other hand, when the content of the solid epoxy resin exceeds 5.0 parts by weight based on the liquid epoxy resin, it may be disadvantageous in terms of compatibility with the thermoplastic resin and reactivity.

In addition, the epoxy resin may further include at least one epoxy resin selected from the group consisting of a cresol novolac type of epoxy resin having a softening point of 50° C. to 100° C. and a bisphenol A epoxy resin having a softening point of 50° C. to 100° C. together with a biphenyl-based epoxy resin having a softening point of 50° C. to 100° C.

Herein, the epoxy resin may include 0.25 to 1.25, or 0.3 to 1.1, parts by weight of the at least one epoxy resin selected from the group consisting of a cresol novolac type of epoxy resin having a softening point of 50° C. to 100° C. and a bisphenol A epoxy resin having a softening point of 50° C. to 100° C. based on the biphenyl-based epoxy resin having a softening point of 50 □ to 100 □.

The epoxy resin may have an average epoxy equivalent weight of 100 to 1000. The average epoxy equivalent weight can be obtained based on the weight ratio of each epoxy resin contained in the epoxy resin and the epoxy equivalent weight.

The type of the thermoplastic resin is not particularly limited, and for example, at least one polymer resin selected from the group consisting of polyimide, polyether imide, polyester imide, polyamide, polyether sulfone, polyether ketone, polyolefin, polyvinyl chloride, phenoxy, a reactive butadiene acrylonitrile copolymer rubber, and a (meth) acrylate-based resin may be used.

Preferably, the thermoplastic resin may be a (meth)acrylate-based resin having a glass transition temperature of −10 to 30° C. and a weight average molecular weight of 200,000 to 1,000,000 g/mol.

The acrylate-based resin is an acrylic copolymer containing an epoxy group, and may contain glycidyl acrylate or glycidyl methacrylate in an amount of 1 to 25 wt %, 2 to 20 wt %, or 2.5 to 15 wt %.

Herein, when the epoxy group is contained in an amount of less than 1 wt % in the (meth)acrylate-based resin, compatibility with the epoxy resin and adhesive strength may not be sufficient. When the amount exceeds 25 wt %, a rising rate of viscosity due to curing becomes too fast, so that bonding and filling of solder bumps may not be sufficiently performed in the thermo-compression bonding process of semiconductor devices.

The thermoplastic resin may be included in an amount of 10 to 1500 parts by weight based on 100 parts by weight of the thermosetting resin in consideration of flow control of the composition during the production of the adhesive film.

As the curing agent, a compound known to be capable of acting as a curing agent for the thermosetting resin may be used. More specifically, the curing agent may include at least one compound selected from the group consisting of an amine-based curing agent and an acid anhydride-based curing agent.

As the curing agent, a novolac-based phenolic resin may be preferably applied.

The novolac-based phenolic resin has a chemical structure in which a ring is located between the reactive functional groups. Due to the structural characteristic, the novolac-based phenolic resin may further lower hygroscopicity of the adhesive composition and may further improve stability in an IR reflow process at a high temperature, thereby preventing peeling of the adhesive film and reflow cracking.

Specific examples of the novolac-based phenolic resin include at least one selected from the group consisting of a novolac phenolic resin, a xyloc novolac phenolic resin, a cresol novolac phenolic resin, a biphenyl novolac phenolic resin, a bisphenol A novolac phenolic resin, and a bisphenol F novolac phenolic resin.

The novolac-based phenolic resin may have a softening point of 60° C. or higher, 60° C. to 150° C., 105° C. to 150° C., or 70° C. to 120° C. The novolac-based phenolic resin having a softening point of 60° C. or higher ensures sufficient heat resistance, strength, and adhesiveness after curing of the adhesive composition. However, when the softening point of the novolac-based phenolic resin is too high, flowability of the adhesive composition may be lowered and voids may be formed inside the adhesive in the actual semiconductor manufacturing process, thereby significantly lowering the reliability or quality of the final product.

The novolac-based phenolic resin may preferably have a hydroxyl equivalent weight of 80 g/eq. to 300 g/eq. and a softening point of 60° C. to 150° C.

The content of the curing agent may be appropriately selected in consideration of physical properties of the finally produced adhesive film. For example, the curing agent may be used in an amount of 10 to 700 parts by weight or 30 to 300 parts by weight based on 100 parts by weight of the thermosetting resin.

The adhesive resin composition for bonding semiconductors may further include a curing catalyst.

The curing catalyst functions for facilitating the action of the curing agent or the curing of the adhesive resin composition for bonding semiconductors, and any curing catalysts known to be used in the field of the adhesive film for semiconductors may be applied without particular limitations.

For example, as the curing catalyst, at least one selected from the group consisting of a phosphorus-based compound, a boron-based compound, a phosphorous-boron-based compound, and an imidazole-based compound may be used. The amount of the curing catalyst may be appropriately selected considering properties of the finally produced adhesive film, and the like.

Meanwhile, the adhesive resin composition for bonding semiconductors of the embodiment may further include an inorganic filler.

The inorganic filler may be at least one inorganic particle selected from the group consisting of alumina, silica, barium sulfate, magnesium hydroxide, magnesium carbonate, magnesium silicate, magnesium oxide, calcium silicate, calcium carbonate, calcium oxide, aluminum hydroxide, aluminum nitride, and aluminum borate.

An ion adsorbent capable of adsorbing ionic impurities and improving reliability may be used as the inorganic filler. The ion adsorbent may be at least one inorganic particle selected from the group consisting of magnesium hydroxide, magnesium carbonate, magnesium silicate, magnesium oxide, calcium silicate, calcium carbonate, calcium oxide, alumina, aluminum hydroxide, aluminum nitride, aluminum borate whisker, a zirconium-based inorganic substance, and an antimony-bismuth-based inorganic substance.

The inorganic filler may preferably have an average particle diameter (based on the longest outer diameter) of 0.01 to 10 μm, 0.02 to 5.0 μm, or 0.03 to 2.0 μm. When the particle diameter of the inorganic filler is too small, it can be easily agglomerated in the adhesive composition. On the other hand, when the particle diameter of the inorganic filler is too large, a semiconductor circuit may be damaged by the inorganic filler and adhesion of the adhesive film may be deteriorated.

The content of the inorganic filler may be 10 to 300 parts by weight or 15 to 250 parts by weight based on 100 parts by weight of a total amount of the thermosetting resin and the thermoplastic resin.

The adhesive composition for semiconductor circuit connection may include 10 to 90 parts by weight of an organic solvent based on 100 parts by weight of a total amount of the thermosetting resin, the thermoplastic resin, and the inorganic filler. The content of the organic solvent may be appropriately selected in consideration of physical properties of the adhesive composition and the finally produced adhesive film, and the manufacturing process.

The organic solvent may be at least one compound selected from the group consisting of esters, ethers, ketones, aromatic hydrocarbons, and sulfoxides.

Examples of the ester solvent include ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, gamma-butyrolactone, epsilon-caprolactone, delta-valerolactone, alkyl oxyacetate such as methyl oxyacetate, ethyl oxyacetate, butyl oxyacetate (e.g., methyl methoxyacetate, ethyl methoxyacetate, butyl methoxyacetate, methyl ethoxyacetate, ethyl ethoxyacetate, etc.), alkyl ester 3-oxypropionate such as methyl 3-oxypropionate, ethyl 3-oxypropionate (e.g., methyl 3-methoxypropionate, ethyl 3-methoxypropionate, methyl 3-ethoxypropionate, ethyl 3-ethoxypropionate, etc.), alkyl ester 2-oxypropionate such as methyl 2-oxypropionate, ethyl 2-oxypropionate, propyl 2-oxypropionate (e.g., methyl 2-methoxypropionate, ethyl 2-methoxypropionate, propyl 2-methoxypropionate, methyl 2-ethoxypropionate, ethyl 2-ethoxypropionate, etc.), methyl 2-oxy-2-methylpropionate, ethyl 2-oxy-2-methylpropionate (e.g., methyl 2-methoxy-2-methylpropionate, ethyl 2-ethoxy-2-methylpropionate, etc.), methyl pyruvate, ethyl pyruvate, propyl pyruvate, methyl acetoacetate, ethyl acetoacetate, methyl 2-oxobutanoate, ethyl 2-oxobutanoate, and the like.

Examples of the ether solvent include diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, and the like.

Examples of the ketone solvent include methyl ethyl ketone, cyclohexanone, cyclopentanone, 2-heptanone, 3-heptanone, N-methyl-2-pyrrolidone, and the like.

Examples of the aromatic hydrocarbon solvent include toluene, xylene, anisole, limonene, and the like.

Examples of the sulfoxide solvent include dimethyl sulfoxide and the like.

The adhesive resin composition for bonding semiconductors may further include a coupling agent. The coupling agent is not particularly limited, but is preferably 2-(3,4-epoxycyclohexyl)-ethyltrimethoxysilane, 3-glycidoxypropyltrimethoxysilane, 3-glycidoxypropylmethyl-diethoxysilane, 3-glycidoxypropyltriethoxysilane, N-2(aminoethyl)3-aminopropylmethyldimethoxysilane, N-2(aminoethyl)3-aminopropyltrimethoxysilane, N-2(aminoethyl)3-aminopropyltriethoxysilane, 3-aminopropyltrimethoxysilane, 3-aminopropyltriethoxysilane, 3-triethoxysilyl-N-(1,3-dimethyl-butylidene) propylamine, N-phenyl-3-aminopropyltrimethoxysilane, mercapto-containing 3-mercaptopropylmethyldimethoxysilane, 3-mercaptopropyltrimethoxysilane, and the like.

According to another embodiment of the present disclosure, an adhesive film for semiconductor circuit connection including the adhesive composition is provided.

Since the adhesive film for semiconductor circuit connection includes the adhesive composition for semiconductor circuit connection of the above-described embodiment, it not only exhibits excellent storage stability at room temperature but can also be cured within a short period of time at a high temperature during thermo-compression bonding.

The adhesive film may have a melt viscosity of 3000 to 6000 Pa·s at a shear rate of 5 rad/s.

Herein, the melt viscosity is defined as the minimum viscosity that can be obtained in the entire range of the adhesive film, not the viscosity at a specific temperature. For example, the lowest viscosity value measured at a rate of 10° C./min with a shear rate of 5 rad/s using TA's advanced rheometric expansion system (ARES) can be defined as the melt viscosity.

The melt viscosity can vary depending on the type of resin, the content of acrylic resin, the type and content of filler, and the like. Since the adhesive film includes the adhesive composition for semiconductor circuit connection of the above-described embodiment, the adhesive film may have a relatively low melt viscosity value as compared with the conventional adhesive film.

This is because the adhesive composition includes the compound of Chemical Formula 1 that is capable of hydrogen bonding in the molecular structure. The compound of Chemical Formula 1 contains an organic functional group including a functional group capable of hydrogen bonding to retard the initiation temperature of the reaction so that an onset point of the reaction moves therewith, and it becomes possible to have a relatively low melt viscosity as compared with the conventional adhesive film. In the case of not including the catalyst of the above Chemical Formula 1 that is capable of hydrogen bonding in the molecular structure, there is no delay effect of the reaction, so that the reaction starts at a lower temperature and the melt viscosity increases, thereby having a relatively high melt viscosity.

Such a change in melt viscosity may affect properties of the entire film, such as possibility of bonding with a non-conductive film (NCF) and possibility of electrical conduction.

The adhesive film may have a change in peak ($\Delta H$) of 20% or less after being allowed to stand at 25° C. for 4 weeks as compared with an initial reaction peak, or may have a change in melt viscosity at a shear rate of 5 rad/s of 50% or less after being allowed to stand at 25° C. for 4 weeks as compared with an initial melt viscosity.

Herein, the change in peak ($\Delta H$) can be calculated by a change in the reaction peak value measured by a differential thermal analyzer (DSC). The change in melt viscosity can be calculated by a change in the melt viscosity measured using the above-described minimum melt viscosity measuring method.

When the change in peak ($\Delta H$) of the adhesive film is 20% or less, or when the change in melt viscosity is 50% or less, the change at room temperature is small and thus storage stability is excellent. Accordingly, a normal process can be performed even after being allowed to stand for a long time at room temperature.

As a supporting substrate for supporting the film, a resin film that is excellent in heat resistance and chemical resistance; a cross-linked film obtained by cross-linking a resin constituting the resin film; or a film obtained by coating a silicone resin or the like on a surface of the resin film and peeling the film may be used.

Examples of the resin constituting the resin film include polyolefins such as polyester, polyethylene, polypropylene, polybutene, and polybutadiene, vinyl chloride, an ethylene-methacrylic acid copolymer, an ethylene-vinyl acetate copolymer, polyester, polyimide, polyethylene terephthalate, polyamide, polyurethane, and the like.

A thickness of the supporting substrate is not particularly limited, but may be 3 to 400 μm, 5 to 200 μm, or 10 to 150 μm.

The adhesive layer is composed of the above-mentioned adhesive composition. The description of the adhesive composition is as described above.

Further, if necessary, the tacky layer may be interposed between the supporting substrate and the adhesive layer. As the tacky layer, those known in the art may be applied without particular limitation.

The kind of the protective film is not particularly limited, and a plastic film known in the art may be applied. For example, the protective film may be a plastic film including a resin such as low density polyethylene, linear polyethylene, medium density polyethylene, high density polyethylene, ultra low density polyethylene, a random copolymer of polypropylene, a block copolymer of polypropylene, a homopolypropylene, a polymethylpentene, an ethylene-vinyl acetate copolymer, an ethylene-methacrylic acid copolymer, an ethylene-methyl methacrylate copolymer, an ethylene-ionomer copolymer, an ethylene-vinyl alcohol copolymer, polybutene, and styrene.

The adhesive film for semiconductor circuit connection may be produced by mixing components of the adhesive composition, coating the same on a supporting substrate to a predetermined thickness to form an adhesive layer, and drying the adhesive layer.

The adhesive film may be produced by forming an adhesive layer on the supporting substrate and then laminating a protective film on the adhesive layer.

The adhesive film may be produced by forming a tacky layer on the supporting substrate, and then sequentially laminating an adhesive layer and a protective film on the tacky layer.

The adhesive layer may be formed on the supporting substrate by a method in which the adhesive composition is coated on the supporting substrate or on a release film directly or after being diluted with an appropriate organic solvent by a known means such as a comma coater, a gravure coater, a die coater, a reverse coater, and the like, followed by drying at a temperature of 60° C. to 200° C. for 10 seconds to 30 minutes.

If necessary, an aging process may be further carried out so as to sufficient advance cross-linking of the adhesive layer.

A thickness of the adhesive layer may be appropriately adjusted in the range of 1 to 500 μm, 5 to 100 μm, or 5 to 50 μm.

Hereinafter, the present invention will be explained in detail with reference to the following examples. However, these examples are only to illustrate the invention, and the scope of the invention is not limited thereto.

Example 1: Preparation of Resin Composition for Bonding Semiconductors and Adhesive Film (1) Preparation of Adhesive Composition for Semiconductor Circuit Connection 40 g of a phenolic resin (KH-6021, manufactured by DIC, bisphenol A novolac resin, hydroxyl equivalent weight of 121 g/eq., softening point of 133° C.) as a curing agent of an epoxy resin; 40 g of a high viscosity liquid epoxy resin (RE-310S, manufactured by Nippon Kayaku Co., bisphenol A epoxy resin, epoxy equivalent weight of 180 g/eq.); 40 g of a thermoplastic acrylate resin (KG-3015, Mw of 900,000, glass transition temperature of 10° q; 1.5 g of 2-(1H-imidazol-2-yl)benzoic acid (manufactured by Sigma-Aldrich); and 80 g of an inorganic filler (SC-2050, manufactured by Admatech, spherical silica, average particle diameter of about 400 nm) were mixed with methyl ethyl ketone to obtain an adhesive composition for semiconductor circuit connection (solids content of 40 wt %).

(2) Preparation of Adhesive Film

The adhesive composition was coated on a release-treated polyethylene terephthalate film (thickness: 38 μm) using a comma coater and dried at 110° C. for 3 minutes to obtain an adhesive film in which an adhesive layer having a thickness of about 20 μm is formed.

(3) Preparation of Semiconductor Device

A wafer including a bump chip (4.5 mm×4.5 mm) as a semiconductor element in which a lead-free solder is formed at a height of 3 μm on a copper filler having a height of 15 μm and a pitch of 50 μm was prepared.

After the adhesive layer of the adhesive film was positioned on a bump surface of the wafer, vacuum lamination was carried out at 50° C. and individualized for each chip.

The individualized bump chip was subjected to thermo-compression bonding on a 6 mm×8 mm substrate chip having a 50 μm pitch connection pad using a thermo-compression bonder. Specifically, it was pre-bonded at 100 N for 2 seconds at a head temperature of 100° C., allowed to stand at 100° C. for 10 minutes, heated to a head temperature of 260° C. for an instant, and subjected to thermo-compression bonding at 100N for 4 seconds.

Examples 2 to 3 and Comparative Examples 1 to 4

An adhesive composition for semiconductor circuit connection and an adhesive film using the adhesive composition were prepared in the same manner as in Example 1, except that the components and the contents shown in Tables 1 and 2 were applied. Thereafter, a semiconductor device was manufactured by using them.

TABLE 1

| Weight (g) | | Example 1 | Example 2 | Example 3 |
|---|---|---|---|---|
| Phenolic resin | KH-6021 | 40 | 40 | 40 |
| Epoxy resin | RE-310S | 40 | 40 | 40 |
| Acrylic resin | KG-3015 | 40 | 40 | 40 |
| Chemical Formula 1-1 | | 1.5 | — | — |
| Chemical Formula 1-2 | | — | 1.5 | — |
| Chemical Formula 1-3 | | — | — | 1.5 |
| Coupling agent | KBM-403 | 1 | 1 | 1 |
| Filler | SC-2050 | 80 | 80 | 80 |

TABLE 2

| Weight (g) | | Comp. Ex. 1 | Comp. Ex. 2 | Comp. Ex. 3 | Comp. Ex. 4 |
|---|---|---|---|---|---|
| Phenolic resin | KH-6021 | 40 | 40 | 40 | 40 |
| Epoxy resin | RE-310S | 40 | 40 | 40 | 40 |
| Acrylic resin | KG-3015 | 40 | 40 | 40 | 40 |
| Catalyst | 2MZ-H | 1.5 | — | — | — |
| | 2PZ | — | 1.5 | — | — |
| | 2-(2-methylphenyl)-1H-imidazole | — | — | 1.5 | — |
| | 3-(1H-imidazol-2-yl)benzoic acid | — | — | — | 1.5 |
| Coupling agent | KBM-403 | 1 | 1 | 1 | 1 |
| Filler | SC-2050 | 80 | 80 | 80 | 80 |

*KH-6021: Phenolic resin (DIC, hydroxyl equivalent weight of 121 g/eq., softening point of 133° C.)
*RE-310S: Epoxy resin (manufactured by Nippon Kayaku Co., epoxy equivalent weight of 180 g/eq)
*KG-3015: Acrylic resin (containing 3 wt % of glycidyl methacrylate-based repeating unit, glass transition temperature of 10 □, weight average molecular weight of 900,000)
* Chemical Formula 1-1: 2-(1H-imidazol-2-yl)benzoic acid
* Chemical Formula 1-2: 2-(4,5-dihydro-1H-imidazol-2-yl)phenol
* Chemical Formula 1-3: Methyl 2-(1H-imidazol-2-yl)benzoate
*2MZ-H: Imidazole curing agent (Curezol 2MZ-H, manufactured by SHIKOKU)
*2PZ: Imidazole curing agent (Curezol 2PZ, manufactured by SHIKOKU)
*2-(2-methylphenyl)-1H-imidazole: Imidazole curing agent (manufactured by Aldrich)
*3-(1H-Imidazol-2-yl)benzoic acid: Imidazole curing agent (an isomer of Chemical Formula 1-1, manufactured by Aldrich)
*KBM-403: Coupling agent (epoxy-based, 3-glycidoxypropyl trimethoxysilane, manufactured by Shin-Etsu Chemical Co., Ltd.)
*SC-2050: Filler (manufactured by Admatech, spherical silica, average particle diameter of about 400 nm)

Experimental Example: Evaluation of Physical Properties

Experimental Example (1) Measurement of Melt Viscosity

The adhesive layer obtained in each of the examples and comparative examples was stacked until the thickness became 320 μm, and then laminated using a roll laminator at 60 □. After each specimen was formed into a circular shape with a diameter of 8 mm, the lowest viscosity value measured at a rate of 10° C./min with a shear rate of 5 rad/s using TA's advanced rheometric expansion system (ARES) was defined as the melt viscosity.

(2) Evaluation of DSC Onset

Differential thermal analysis was performed at a rate of 10° C./min in the range of 30 to 300° C. using a differential thermal analyzer (DSC). The temperature at the intersection point of a part at which an initial reaction peak begins to form and an extrapolated baseline was designated as onset.

(3) Evaluation of Voids

For each of the semiconductor devices obtained in the examples and comparative examples, when the area occupied by voids between the bump chip and the substrate chip by Scanning Acoustic Tomography (SAT) was 1% or less, it was evaluated as pass (0). When exceeding 1%, it was evaluated as failure (X).

(4) Evaluation of Conduction

For each of the semiconductor devices obtained in the examples and comparative examples, it was evaluated as pass (0) when daisy chain connection could be confirmed, and failure (X) when daisy chain connection could not be confirmed.

(5) Evaluation of Connection State

For each of the semiconductor devices obtained in the examples and comparative examples, the connection part was exposed by single-side polishing and observed with an optical microscope. When the adhesive composition was not trapped at the connection part and solder was sufficiently wet in the wiring, it was evaluated as pass (0), and the other was evaluated as failure (X).

(6) Evaluation of Aging Property at Room Temperature

The adhesive films obtained in the examples and comparative examples were allowed to stand at 25° C., and the change in peak (LH) was calculated using a differential thermal analyzer (DSC) every day. The change in minimum melt viscosity was measured by the above-described minimum melt viscosity measuring method. When the change in peak (ΔH) was more than 20% and the change in minimum melt viscosity was more than 50%, it was evaluated that there was a change with time. When no change with time was observed over 4 weeks, it was evaluated as pass (O). And when there was a change with time within 4 weeks, it was evaluated as failure (X).

TABLE 3

|  | Example 1 | Example 2 | Example 3 |
|---|---|---|---|
| Melt viscosity (Pa · s) | 4300 | 3800 | 4100 |
| DSC onset (° C.) | 157 | 161 | 153 |
| Voids | ○ | ○ | ○ |
| Conduction | ○ | ○ | ○ |
| Connection state | ○ | ○ | ○ |
| Aging property at room temperature | ○ | ○ | ○ |

TABLE 4

|  | Comp. Ex. 1 | Comp. Ex. 2 | Comp. Ex. 3 | Comp. Ex. 4 |
|---|---|---|---|---|
| Melt viscosity (Pa · s) | 11,200 | 9200 | 9000 | 6200 |
| DSC onset (° C.) | 97 | 105 | 110 | 121 |
| Voids | X | X | X | X |
| Conduction | X | X | X | Δ |
| Connection state | X | X | X | Δ |
| Aging property at room temperature | X | X | X | X |

As shown in Tables 3 and 4, it was confirmed that the adhesive films for semiconductors provided in Examples 1 to 3 had a relatively low melt viscosity and a high DSC onset temperature.

This may be because the compositions of Examples 1 to 3 have a high DSC onset temperature so that substantially no micro-reaction occurs at a temperature of the drying process during coating and thus can have a relatively low viscosity. Accordingly, in the semiconductor device to which the adhesive films of Examples 1 to 3 were applied, voids did not substantially remain, and the change in peak (LH) was small during the time at which the film was allowed to stand for 10 minutes after being pre-bonded at 100° C. As a result, it was confirmed that no change with time occurred, and no conduction defect or poor connection state occurred.

On the contrary, since the onset of the adhesive compositions provided in the comparative examples was low, the micro-reaction proceeded at a temperature of the drying process during coating to form a high viscosity. As a result, it was confirmed that voids were likely to remain in the semiconductor device to which the adhesive films of the comparative examples were applied, and conduction defect and poor connection state occurred due to the change with time during the time at which the film was allowed to stand for 10 minutes after being pre-bonded at 100° C. In addition, it was confirmed that the adhesive films of the comparative examples rapidly reacted even when stored at room temperature, and thus the change with time occurred within 4 weeks.

The invention claimed is:

1. An adhesive resin composition for bonding semiconductors, comprising: a thermoplastic resin; a thermosetting resin; a curing agent; and a compound represented by Chemical Formula 1 or 2-(4,5-Dihydro-1H-imidazol-2-yl)phenol:

[Chemical Formula 1]

$$\text{imidazole-phenyl structure with } R_1, R_2, (R_3)_n$$

wherein in the Chemical Formula 1, $R_1$ is hydrogen, a C1 to C10 alkyl group, or a C6 to C20 aryl group, $R_2$ is a carboxyl group, a carbonyl group, a formyl group, or an amine group, $R_3$ is hydrogen, a halogen, a C1 to C10 alkyl group, or a C6 to C20 aryl group, and n is 1 to 4.

2. The adhesive resin composition for bonding semiconductors of claim 1, wherein in the Chemical Formula 1, $R_1$ is hydrogen or a benzene group.

3. The adhesive resin composition for bonding semiconductors of claim 1, comprising 0.1 to 15 parts by weight of the compound of Chemical Formula 1 or 2-(4,5-Dihydro-1H-imidazol-2-yl)phenol based on 100 parts by weight of a total amount of the thermoplastic resin; the thermosetting resin; the curing agent; and the compound of Chemical Formula 1 or 2-(4,5-Dihydro-1H-imidazol-2-yl)phenol.

4. The adhesive resin composition for bonding semiconductors of claim 1,
wherein the thermoplastic resin comprises at least one polymer resin selected from polyimide, polyether imide, polyester imide, polyamide, polyether sulfone, polyether ketone, polyolefin, polyvinyl chloride, phenoxy, reactive butadiene acrylonitrile copolymer rubber, and (meth)acrylate-based resin.

5. The adhesive resin composition for bonding semiconductors of claim 1,
wherein the thermosetting resin comprises at least one resin selected from a solid epoxy resin and a liquid epoxy resin.

6. The adhesive resin composition for bonding semiconductors of claim 1,
wherein the curing agent comprises a novolac-based phenolic resin having a softening point of 60° C. to 150° C.

7. An adhesive film for semiconductors, comprising an adhesive layer comprising the adhesive resin composition for bonding semiconductors of claim 1.

8. The adhesive film for semiconductors of claim 7,
wherein the adhesive film has a melt viscosity of 3000 to 6000 Pa s at a shear rate of 5 rad/s.

9. The adhesive film for semiconductors of claim 7,
wherein the adhesive film has a change in peak ($\Delta H$) of 20% or less after being allowed to stand at 25° C. for 4 weeks as compared with an initial reaction peak.

10. The adhesive film for semiconductors of claim 7,
wherein the adhesive film has a change in melt viscosity at a shear rate of 5 rad/s of 50% or less after being allowed to stand at 25° C. for 4 weeks as compared with an initial melt viscosity.

11. The adhesive film for semiconductors of claim 7, wherein the adhesive layer has a thickness of 1 to 500 μm.

12. The adhesive film for semiconductors of claim 7, comprising a supporting substrate including a resin film.

13. The adhesive film for semiconductors of claim 12, wherein the supporting substrate has a thickness of 3 to 400 μm.

14. The adhesive resin composition for bonding semiconductors of claim 1, further comprising an organic solvent.

* * * * *